(12) United States Patent
Zoppetti et al.

(10) Patent No.: US 9,168,229 B2
(45) Date of Patent: *Oct. 27, 2015

(54) SOFT GELATIN CAPSULES

(71) Applicant: ALTERGON S.A., Lugano (CH)

(72) Inventors: Giorgio Zoppetti, Milan (IT); Maurizio Marchiorri, Valbrona (IT)

(73) Assignee: ALTERGON S.A., Lugano (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/246,396

(22) Filed: Apr. 7, 2014

(65) Prior Publication Data

US 2014/0242161 A1    Aug. 28, 2014

Related U.S. Application Data

(62) Division of application No. 11/885,422, filed as application No. PCT/EP2006/060649 on Mar. 13, 2006, now Pat. No. 8,728,519.

(30) Foreign Application Priority Data

Mar. 11, 2005    (IT) .............................. MI2005A0387

(51) Int. Cl.
  A61K 9/64       (2006.01)
  A61K 9/48       (2006.01)
  A61K 47/40      (2006.01)
  A61K 31/355     (2006.01)
  A61K 31/4415    (2006.01)
  A61K 31/51      (2006.01)
  A61K 31/525     (2006.01)
  A61K 31/57      (2006.01)
  A61K 31/593     (2006.01)
  A61K 31/616     (2006.01)
  A61K 31/714     (2006.01)
  A61K 33/04      (2006.01)
  A61K 33/08      (2006.01)
  A61K 33/10      (2006.01)
  A61K 33/18      (2006.01)
  A61K 33/30      (2006.01)

(52) U.S. Cl.
  CPC ............ *A61K 9/4825* (2013.01); *A61K 31/355* (2013.01); *A61K 31/4415* (2013.01); *A61K 31/51* (2013.01); *A61K 31/525* (2013.01); *A61K 31/57* (2013.01); *A61K 31/593* (2013.01); *A61K 31/616* (2013.01); *A61K 31/714* (2013.01); *A61K 33/04* (2013.01); *A61K 33/08* (2013.01); *A61K 33/10* (2013.01); *A61K 33/18* (2013.01); *A61K 33/30* (2013.01); *A61K 47/40* (2013.01)

(58) Field of Classification Search
  None
  See application file for complete search history.

(56) References Cited

U.S. PATENT DOCUMENTS

2003/0104048 A1*    6/2003    Patel et al. .................... 424/451

* cited by examiner

*Primary Examiner* — Snigdha Maewall
(74) *Attorney, Agent, or Firm* — Novak Druce Connolly Bove + Quigg LLP

(57) ABSTRACT

The present invention relates to soft gelatin capsules characterized in that the shell includes a cyclodextrin and in that the filling material contains a liposoluble drug capable of forming a complex with said cyclodextrin for improving the solubility of the active ingredient upon disintegration of the soft gelatin capsule.

5 Claims, 1 Drawing Sheet

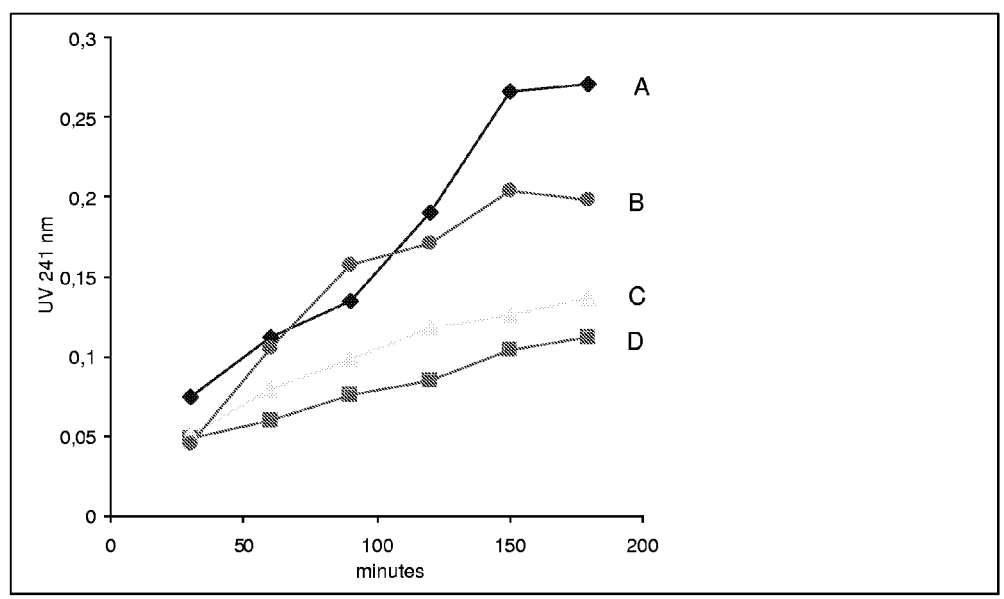

SOFT GELATIN CAPSULES

CROSS REFERENCE TO RELATED APPLICATIONS

This application is a divisional of U.S. patent application Ser. No. 11/885,422, filed on Aug. 29, 2007, and entitled "SOFT GELATIN CAPSULES," which is a §371 national stage entry of International Application No. PCT/EP2006/060649, filed Mar. 13, 2006, and entitled "NEW SOFT GELATIN CAPSULES," which claims priority to Italian Patent Application No. MI2005A000387, filed Mar. 11, 2005, the entireties of which are incorporated herein by reference.

FIELD OF THE INVENTION

The present invention relates to a new formulation for soft gelatin capsules which allows an increase in the bioavailability of poorly water soluble or water insoluble active ingredients.

BACKGROUND ART

The pharmaceutical form known as "soft gelatin capsule" (SEC capsules) is used to administer, mainly orally, non-crystalline and poorly water-soluble active ingredients. For example preparations of progesterone and vitamin complexes are present on the market in the form of soft gelatin capsules.

Soft gelatin capsules are composed of a shell containing plasticized gelatin which encloses a filling material, normally composed of a liquid or semi-liquid lipophilic active ingredient, of a solution of a lipophilic active ingredient or of a pasty product and having characteristics that will not dissolve the shell.

However, these formulations have the drawback of often having reduced efficacy due to poor bioavailability of the active ingredients contained therein.

Cyclodextrins are cyclic sugars which have the particularity of complexing lipophilic molecules, considerably increasing their water solubility. It is known that progesterone and some vitamins form water-soluble complexes with cyclodextrins, that have thus greater bioavailability compared to the corresponding non complexed compounds.

Nonetheless, these complexes cannot be used in the formulation of soft gelatin capsules, since in this case the solution to be encapsulated would have characteristics that cause solubilization of the gelatin of the shell of the capsules thus rendering the formation, or the stability, of the capsule unachievable.

From WO 99/33924 there are known gelatin compositions derived from non-bovine or non-pig, preferably fish origin. To improve the workability, in particular the flowing properties, of the aforementioned "alternative" gelatins, to be employed in the pharmaceutical, veterinary, food or cosmetics field, the incorporation of a setting system comprising hydrocolloids and optionally cations and/or sequestering agents in amounts of less than 5%, preferably 0.01 to 3% is described. Among the sequestering agents employable in the alternative gelatins, also beta-cyclodextrin is mentioned as possible constituent of the setting system.

Japanese Patent No. 62-249935 published in 1987 reports of gelatin substrates containing 10-2% of cyclodextrin, preferably beta-cyclodextrin, displaying improved shelf-life properties, as far as conservation of the so-modified gelatin's disintegration properties is concerned. The preparations employed for the confirmatory tests reported in this publication, do not comprise, however, the inclusion of active principles.

Therefore, the problem remains of developing formulations of soft gelatin capsules which allow the bioavailability of the drugs contained therein to be increased.

SUMMARY OF THE INVENTION

It has now surprisingly been found new formulation in capsule which allows the bioavailability of the poorly soluble active ingredients to be increased. In particular, the present inventors have developed a new soft gelatin capsule consisting of a shell containing a cyclodextrin, preferably selected from β-cyclodextrin and hydroxypropyl-βcyclodextrin (HPβ cyclodextrin), and of a filling material containing a poorly water-soluble or water-insoluble drug and capable of forming a complex with said cyclodextrin. This new formulation shows a stability equivalent to that of conventional soft gelatin capsules and allows to overcome the problem of poor bioavailability of the active ingredients contained therein.

DESCRIPTION OF THE DRAWINGS

FIG. 1 represents the dissolution curves of progesterone, obtained with the method coded by the European Pharmacopoeia, from the capsule prepared in Example 2 (curve A) and from a commercial capsule containing an equal amount of progesterone (curves B-D). With regard to the curves obtained from the commercial capsule, the curve B was obtained with no cyclodextrin in the dissolution medium, while the curves C and D were obtained respectively with 50 and 100 mg of hydroxypropyl-β-cyclodextrin in the dissolution medium.

DETAILED DESCRIPTION OF THE INVENTION

The present invention relates to a soft gelatin capsule consisting of a shell which encloses a filling material (technically called fill) characterized in that the shell contains a cyclodextrin, preferably chosen from β-cyclodextrin and hydroxypropyl-β-cyclodextrin, and the filling material contains a poorly water soluble or water-insoluble active ingredient capable of forming a complex with said cyclodextrin.

Preferably, the shell of the capsule of the present invention contains an amount of cyclodextrin ranging from 1% and 30% in weight.

In particular, according to a preferred embodiment of the present invention, when said cyclodextrin is β-cyclodextrin, this is contained in the shell of the capsule of the present invention in an amount ranging from 1% to 5%, while when said cyclodextrin is hydroxypropyl-β-cyclodextrin, this is contained in the shell of the capsule of the present invention in an amount ranging from 5% to 30%.

The shell of the capsule of the present invention also contains, just as conventional soft gelatin capsules, gelatin, preferably in an amount ranging from 35% and 50% in weight, a plasticizer, preferably in an amount ranging from 15% to 25% in weight and water, preferably in an amount ranging from 4% to 7% in weight.

Preferably, said plasticizer is a polyhydroxyl alcohol, preferably selected from the group consisting of glycerol, sorbitol, sorbitol/sorbitan mixtures, 1-2 propylene glycol, macrogol 200-600 and mixtures thereof.

The filling material of the capsule of the present invention is preferably composed of a solution or suspension of the active ingredient in an oily solvent/phase. The latter is preferably selected from the group consisting of soy, peanut, sunflower, olive, wheat germ and rape oil, beeswax, hydrogenated coconut oil, refined palm oil, glyceryl monostearate (geleol®) and mixtures thereof.

The expression "poorly water soluble or water insoluble active ingredient" according to the present invention indicates active ingredients which have a water solubility of less than 0.1% w/v.

In particular, active ingredients suitable to be incorporated in the capsule of the present invention are, for example, steroid hormones, liposoluble vitamins or, in general, active ingredients having aromatic rings such as many non-steroid anti-inflammatory drugs (NSAID).

According to a particularly preferred application, the capsule of the present invention contains an active ingredient selected from the group consisting of progesterone, liposoluble vitamins, as single vitamins or in mixture with other vitamins and acetylsalicylic acid.

Preferably, when the active ingredient is progesterone, this is contained in the capsule of the present invention in an amount ranging from 10 to 200 mg and even more preferably of 100 mg. Particularly preferred is a capsule wherein the filling material contains the aforesaid amounts of progesterone and the shell contains from 10 to 22 mg, preferably 20 mg, of hydroxypropyl-β-cyclodextrin.

Liposoluble vitamins, as single vitamins or in mixture with other vitamins, are instead contained in the capsules of the present invention preferably in an amount ranging from 0.001 mg to 20 mg, more preferably from 3 to 20 mg and even more preferably of 14 mg. Capsules particularly preferred according to the present invention are those wherein the filling material contains from 3 to 20 mg, preferably 14 mg, of liposoluble vitamins and the shell contains from 1 to 15 mg of β-cyclodextrin. The aforesaid liposoluble vitamins are preferably selected from the group consisting of vitamin D and of vitamins of the B group. Particularly preferred is a mixture of the aforesaid vitamins containing from 5 to 15 μg of vitamin D, from 0.5 to 2 mg of vitamin B1 (Thiamine), from 0.5 to 3 mg of vitamin B2 (Riboflavin), from 0.5 to 2 mg of vitamin B6, from 5 to 20 μg of vitamin B12, from 400 to 800 μg of vitamin A, from 50 to 150 μg of vitamin H (Biotin), from 1 to 10 mg of vitamin E.

According to a further embodiment, the capsules of the present invention contain acetylsalicylic acid in an amount preferably ranging from 50 to 300 mg per dose, preferably of 88.5 mg. Among these, capsules in which the filling material contains from 50 to 300 mg per dose, preferably 88.5 mg, of acetylsalicylic acid and the shell contains from 10 to 150 mg, preferably 55 mg, of hydroxypropyl-β-cyclodextrin are particularly preferred.

The capsules of the present invention are prepared according to the procedures, well known in the art, normally used to prepare soft gelatin capsules, the preferred procedure being the Rotary Die Process.

According to a further embodiment of the capsule of the present invention, if it is desirable for the capsule to pass through the stomach unaltered and only release its content at the level of the intestine, for example in the case of drugs which deteriorate in an acid environment, a gastro-resistant and enteric-soluble coating, preferably polymeric, is applied to the surface of the shell of the capsule, using techniques well known in the art for the preparation of gastro-resistant capsules.

A further object of the present invention is composed of a mix suitable for preparation of the shell of a capsule according to the present invention comprising a cyclodextrin, preferably selected from β-cyclodextrin and hydroxypropyl-β-cyclodextrin, gelatin, a plasticizer and water. Preferably, the plasticizer is a polyhydroxyl alcohol, preferably selected from the group consisting of glycerol, sorbitol, sorbitol/sorbitan mixtures, 1-2 propylene glycol, macrogol 200-600 and mixtures thereof.

Preferably, said mix contains from 0.7% to 20% in weight of cyclodextrin, preferably selected from β-cyclodextrin and hydroxypropyl-β-cyclodextrin, from 20% to 50% in weight of gelatin, from 1% to 25% in weight of a plasticizer and from 20 to 50% in weight of water. According to a preferred embodiment of the present invention, when the aforesaid cyclodextrin is β-cyclodextrin, this is contained in the aforesaid mix in a quantity ranging from 0.1% to 2.5%, while when the aforesaid cyclodextrin is hydroxypropyl-β-cyclodextrin, this is contained in the mix of the present invention in a quantity ranging from 1% to 20%.

The active ingredients contained in the capsule of the present invention have significantly higher bioavailability than that of the same active ingredients administered with conventional soft gelatin capsules.

In fact, upon reaching the stomach, or, in the case of gastro-resistant capsules, the intestine, the capsule of the present invention dissolves in the biological fluids, gradually releasing the cyclodextrin and, once the capsule has been perforated, the content with active ingredient. These two components, also favored by the closeness of the molecules, form a complex which increases the water solubility of the active ingredient thereby improving its bioavailability.

EXAMPLES

Example 1

The solubility of β-, γ and hydroxypropyl-β-(HPβ) cyclodextrin in the solution containing gelatin was verified. This study was conducted by dissolving quantities of 2.5% or of 5% (W/V) of β-, γ or hydroxypropyl-β-(HPβ) cyclodextrin in an aqueous solution containing 36% (W/W) of gelatin and 15% (W/W) of anhydrous glycerin.

The results obtained show that only γ-cyclodextrin and hydroxypropyl-β-cyclodextrin are soluble at 5% in the aforesaid solution, while β-cyclodextrin is soluble in the aforesaid solution at a concentration of 2.5%, while at a concentration of 5% it produces an opalescent mixture.

Therefore, in the evaluation of the tests performed it was decided to continue by using beta cyclodextrin for the capsules with a low cyclodextrin content and using HPβ CD cyclodextrin for those with a high cyclodextrin content.

In the latter case, the maximum solubility obtainable was analyzed by preparing solutions at different concentrations.

The following formulations were taken into consideration:

|  | A | B | C | D | E |
|---|---|---|---|---|---|
| Gelatin | 36% | 36.46% | 36% | 30% | 36% |
| Anhydrous glycerin | 15% | 16.67% | 16% | 13% | 16% |
| HPβ-cyclodextrin | 14% | 15.62% | 18% | 19.5% | 23% |
| Water | 35% | 31.25% | 30% | 37.5% | 25% |

At all the concentrations tested solubilization of the HPβ-cyclodextrin in the gelatin formulation was observed.

The results obtained show that among the formulations tested, E is the only one that presents rheological characteristics unsuitable for processing, in particular as it shows excessive adhesiveness that renders it unusable to prepare soft gelatin capsules. On the contrary, all other formulations show suitable Theological characteristics. In particular, formulation D appears to be the one with the greatest amount of HPβ-cyclodextrin that is usable.

Example 2

Preparation of Soft Gelatin Capsules with High Cyclodextrin Content Containing Progesterone.

a) Preparation of the Mix for the Shell 25.9 liters of purified water are added to 13.65 kg of HPβ-cyclodextrin (Kleptose HP-β by Roquette Freres—Fr) and kept under stirring for 15-60 minutes at 30° C. When a limpid solution is obtained 9.1 kg of anhydrous glycerin are added, continuing the stirring, and the temperature is brought to 70° C., then 21 kg of gelatin are added and the mixture obtained is kept under stirring for 15-60 minutes. The mass is then deaerated by applying a progressive vacuum until reaching a value ranging from −0.8 to −0.9 bar.

b) Preparation of the Progesterone Filling Material

The following formulation was prepared:

| Progesterone | 100 mg |
| Peanut oil and soy lecithin | qs to 250 mg | c) Preparation of the Capsules

Oval, size 5 soft gelatin capsules were prepared according to the process known as Rotary Die Process.

Capsules with the following characteristics were obtained:
mean weight per capsule: 418 mg
residual humidity: 5.8
progesterone content: 96.3 mg/capsule
disintegration time, measured according to the method coded by the European Pharmacopoeia: 15 minutes

Example 3

Preparation of Soft Gelatin Capsules with a High Cyclodextrin Content Containing Acetylsalicylic Acid a) Preparation of the Mix for the Shell The mix for the shell was prepared as described in Example 2.

b) Preparation of the Filling Material Containing Acetylsalicylic Acid

The following formulation was prepared:

| acetylsalicylic acid | 100 mg |
| excipients | qs to 402 mg |

(Epax 5500 TG, soy lecithin, beeswax, hydrogenated coconut oil, refined palm oil, delta tocopherol).

c) Oval, Size 7.5 Soft Gelatin Capsules were Prepared According to the Process Known as Rotary Die Process.

Capsules having the following characteristics were obtained:
mean weight per capsule: 644 mg
residual humidity, according to the Karl Fisher method: 5.3%
acetylsalicylic acid content: 88.56 mg/capsule
dissolution time, measured according to the European Pharmacopoeia method: 15 minutes

Example 4

Preparation of Soft Gelatin Capsules with a Low Cyclodextrin Content Containing a Multivitamin Complex a) Preparation of the Mix for the Shell 23 liters of purified water (including an additional dose of 5 l) are added to 1.00 kg of beta cyclodextrin (Cavasol W7 by Roquette Freres—France) and kept under stirring until completely dissolved at 70° C. When a limpid solution is obtained, 1.0 kg of anhydrous glycerin and, subsequently, 21.7 kg of gelatin are added. The mass is then deaerated by applying a progressive vacuum to eliminate excess water.

b) Preparation of the Filling Material Containing the Multivitamin Compound

The following formulation was prepared:

| Heavy calcium carbonate | 125 mg |
| Heavy magnesium oxide | 149 mg |
| Zinc sulphate monohydrate | 20.550 mg |
| Vit E Nat. | 7.452 mg |
| Vit D3 in oil (1 MIO IU/GR) | 0.240 mg |
| Vit. B1 (Thiamine mononitrate) | 0.600 mg |
| Vit. B2 (Riboflavin) | 0.770 mg |
| Vit. B6 (Pyridoxine HCl) | 0.805 mg |
| Vit. B12 0.1% | 2.400 mg |
| Potassium iodide | 0.100 mg |
| Selenium yeast (2000 mcg/g) | 25.00 mg |

GMO-free soy oil, Geleol, GMO-free soy lecithin, qs to 655.561 mg c) Preparation of the Soft Capsules The aforesaid preparations were subsequently utilized to produce oval size 10 soft capsules, according to the process known as Rotary Die Process.

Soft capsules with the following characteristics were obtained:
mean weight per capsule: 88 mg
residual humidity: 5.4%
multivitamin complex content: 680 mg/capsule

Example 5

The capsule containing progesterone obtained according to Example 2 was analyzed with the dissolution method according to the European Pharmacopoeia in comparison with a commercial soft gelatin capsule containing 100 mg of progesterone (Utrogestran).

Aliquots of solution were taken at regular intervals and analyzed under UV light at 241 nm.

The results obtained are set down in FIG. 1.

As can be seen from the figure, dissolution of the progesterone from utrogestran is very modest, due to the almost total insolubility in water of this active ingredient.

On the contrary, the capsule of the present invention allows to obtain a dissolution of quantities of progesterone five times greater compared to utrogestran.

The effect observed is surprisingly greater than the one obtained from utrogestran by adding hydroxypropyl cyclodextrin to the dissolution medium at the same dosage of the capsule in Example 2 (50 mg) or at double the dosage (100 mg).

We claim:

1. A soft gelatin capsule consisting of a shell with a gastro-resistant and enteric-soluble coating enclosing a filling material, wherein:
    the filling material consists of a solution of a poorly water-soluble or water-insoluble active ingredient in an oily solvent phase,
    the shell contains a cyclodextrin which is thus maintained separated from the active ingredient in the filling material, the shell of the capsule is prepared from a mix containing, by weight:
- from 0.7 to 20% of hydroxypropyl-β-cyclodextrin, or β-cyclodextrin,
- from 20 to 50% by weight of gelatin,
- from 1 to 25% by weight to a plasticizer,
- from 20 to 50% by weight of water, where the active ingredient is selected from the group consisting of non-steroid anti-inflammatory drugs having aromatic rings.

2. The soft gelatin capsule as claimed in claim 1, wherein the plasticizer contained in the shell of the capsule is a polyhydroxyl alcohol.

3. The soft gelatin capsule as claimed in claim 2, wherein the plasticiser is selected from the group composed of glycerol, sorbitol, sorbitol/sorbitan mixtures, 1-2 propylene glycol, macrogol 200-600 and mixtures thereof.

4. The soft gelatin capsule as claimed in claim 1, wherein said oily solvent/phase is selected from the group consisting of soy, peanut, sunflower, olive, wheat germ and rape oil, beeswax, hydrogenated coconut oil, refined palm oil, glyceryl monostearate and mixtures thereof.

5. The soft gelatin capsule as claimed in claim 1, wherein the shell of the capsule is coated with a gastro-resistant and enteric-soluble coating.

* * * * *